(12) United States Patent
McMillan (10) Patent No.: US 8,774,497 B2
(45) Date of Patent: Jul. 8, 2014

(54) METHOD FOR LOCATING ARTEFACTS IN A MATERIAL

(75) Inventor: Alison J McMillan, Uttoxeter (GB)

(73) Assignee: Rolls-Royce PLC, London (GB)

(*) Notice: Subject to any disclaimer, the term of this patent is extended or adjusted under 35 U.S.C. 154(b) by 204 days.

(21) Appl. No.: 13/571,087

(22) Filed: Aug. 9, 2012

(65) Prior Publication Data
US 2013/0044941 A1   Feb. 21, 2013

(30) Foreign Application Priority Data

Aug. 17, 2011 (GB) .................................. 1114111.6

(51) Int. Cl.
*G06K 9/00* (2006.01)

(52) U.S. Cl.
CPC ....................................... *G06K 9/00* (2013.01)
USPC .................. 382/154; 378/4; 378/20; 378/38; 378/57

(58) Field of Classification Search
CPC ............ A61F 2310/00215; A61F 2002/30092; G01N 2291/0231; G01N 2291/0289; G01N 21/9501; G01N 23/046; G01N 2291/106; H04N 19/0026; G06T 15/00; G06T 7/004; G06K 9/34; B29C 47/0004; B29C 43/003
USPC ............................... 382/154; 378/4, 20, 38, 57
See application file for complete search history.

(56) References Cited

U.S. PATENT DOCUMENTS

| | | | | |
|---|---|---|---|---|
| 4,920,491 A | * | 4/1990 | Eberhard et al. | 382/131 |
| 5,159,642 A | * | 10/1992 | Kosaka | 382/134 |
| 5,428,655 A | * | 6/1995 | Moriya et al. | 378/4 |
| 5,953,013 A | * | 9/1999 | Shimizu | 345/419 |
| 6,002,739 A | * | 12/1999 | Heumann | 378/8 |
| 6,324,243 B1 | * | 11/2001 | Edic et al. | 378/4 |
| 6,384,872 B1 | * | 5/2002 | Tsui et al. | 348/625 |
| 7,268,925 B1 | * | 9/2007 | Green | 358/486 |
| 2004/0013294 A1 | * | 1/2004 | De Man et al. | 382/132 |
| 2004/0218715 A1 | | 11/2004 | Jones | |
| 2004/0248144 A1 | * | 12/2004 | Mir | 435/6 |
| 2005/0075846 A1 | | 4/2005 | Kim | |
| 2005/0098915 A1 | * | 5/2005 | Long et al. | 264/109 |
| 2005/0152504 A1 | | 7/2005 | Shih | |
| 2007/0092654 A1 | * | 4/2007 | Smith et al. | 427/346 |
| 2008/0022774 A1 | * | 1/2008 | Lu | 73/606 |
| 2010/0131210 A1 | | 5/2010 | Fingerhut et al. | |
| 2011/0019796 A1 | | 1/2011 | Wuestenbecker et al. | |

FOREIGN PATENT DOCUMENTS

| | | |
|---|---|---|
| EP | 2 246 820 A1 | 11/2010 |
| WO | WO 2005/093404 A2 | 10/2005 |
| WO | WO 2010/041005 A2 | 4/2010 |

OTHER PUBLICATIONS

British Search Report in British Application No. 1114111.6 dated Nov. 22, 2011.

* cited by examiner

*Primary Examiner* — Vu Le
*Assistant Examiner* — Aklilu Woldemariam
(74) *Attorney, Agent, or Firm* — Oliff PLC (57) ABSTRACT

A method for locating artifacts, such as particles or voids, in a material includes the steps of defining a path through a volume of the material, sensing the presence and type of any artifacts along the path and determining for each sensed artifact, the respective distance along the path. Analysis of the quantity of sensed artifacts and their respective position along the path enables the determination of measures for the artifact density, artifact size and artifact distribution in the material.

12 Claims, 5 Drawing Sheets

9 x 9 Pixels

METHOD FOR LOCATING ARTEFACTS IN A MATERIAL

This invention claims the benefit of UK Patent Application No. 1114111.6, filed on 17 Aug. 2011, which is hereby incorporated herein in its entirety.

FIELD OF THE INVENTION

This invention relates to a method for locating artefacts in a material and particularly, but not exclusively, to a method for locating artefacts in a composite material. These artefacts may include filler particles or other inclusions, or may include structural features such as voids.

BACKGROUND TO THE INVENTION

It is known that engineered components may contain features (such as crystal phases in polycrystalline metallic components) or defects (such as slag particles in steel parts) which arise as a consequence of their manufacturing or fabrication.

Although characterisation of the bulk properties of the material can be performed, it can be difficult to quantify the direct effect of these defects on the mechanical properties of the component, particularly where the component is made from a composite material.

Large flaws in the component are likely to be easily spotted by visual or basic inspection or else are excluded through optimisation of the manufacturing process. In practice, this means that it is only the smaller flaws that present a concern. Depending on the type of component, the smaller flaws may also be effectively excluded (by being reduced to a statistically insignificant quantity) through careful management of the manufacturing process.

It is known to implement some type of quality assurance (QA) process in order to assess the quality of the manufacturing process and to determine the components' suitability for use. This process generally involves taking sample components from each manufacturing batch which are then sectioned in various orientations to check for voids or other flaws.

If a void or flaw is discovered in the sample, the entire batch of components from which the sample has been drawn will then be scrapped, or possibly reworked. This can result in the unnecessary scrapping or rework of components which may not exhibit the same actual flaws.

An alternative QA process involves the inspection of every item manufactured using a non-destructive technique, such as, for example, ultrasound or computer tomography (CT) methods. This will likely be more expensive to implement than the above-mentioned sampling method but may be appropriate for high value components or where manufacturing process stability is hard to achieve.

An example of a situation where manufacturing process stability can be problematic is the use of resin transfer moulding techniques where the resin itself has a finite shelf life. The shelf life reflects that fact that the resin is slowly curing from the point at which it is used for the first components in a batch and the end of the batch. As a result, the viscosity of the resin is slowly increasing which requires higher pressures to inject the resin into the component during its manufacture. This in turn can result in increasing levels of porosity from the first to the last components in a particular batch.

Consequently, a QA process in which resin injection pressure alone is monitored will not provide reliable indication of component quality and hence suitability for use.

Existing QA processes, whether destructive or non-destructive, generally involve ensuring that all flaws are below a threshold size or the total number of flaws (usually expressed in terms of the material's porosity) is below a limiting value. Both of these measures are generally impossible to measure directly.

The threshold size is generally set at a high level in order that it can be evaluated from flaws seen at the surface of the component.

Porosity on the other hand may be evaluated from pre-determined correlation with ultrasound absorption levels and can thus be inferred from ultrasound scanning of the component.

However, such an approach does not identify the distribution of flaws in the component, for example by identifying clusters of flaws which can make the component unserviceable.

Figure 1A:
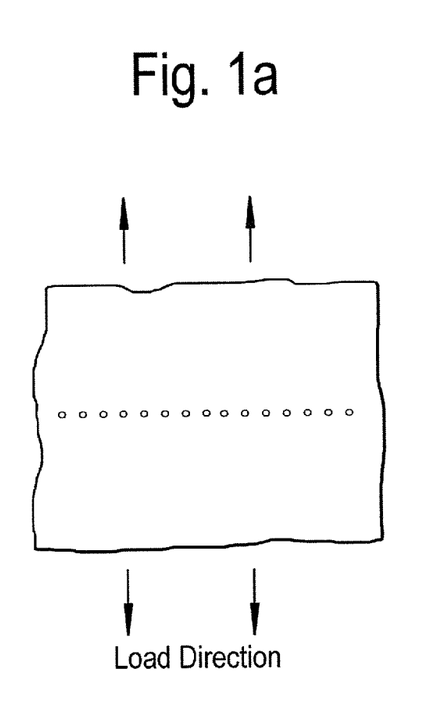
FIG. 1a is a schematic view of a material having a linear distribution of a plurality of artefacts in the form of voids.
Figure 1B:
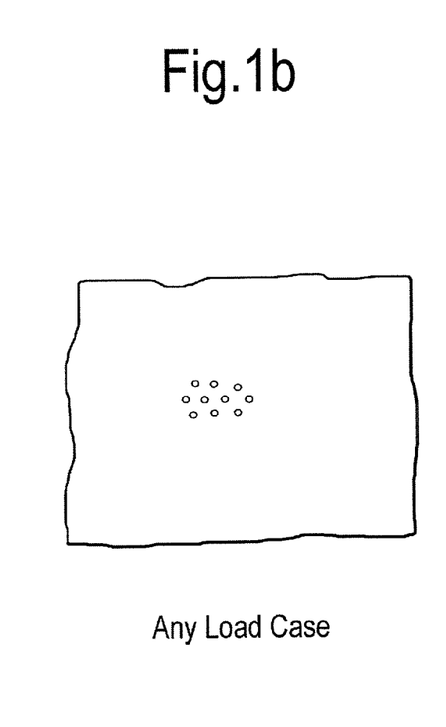
FIG. 1b is a schematic view of a material having a plurality of voids which are grouped together in a single central portion of the material.
Figure 1C:
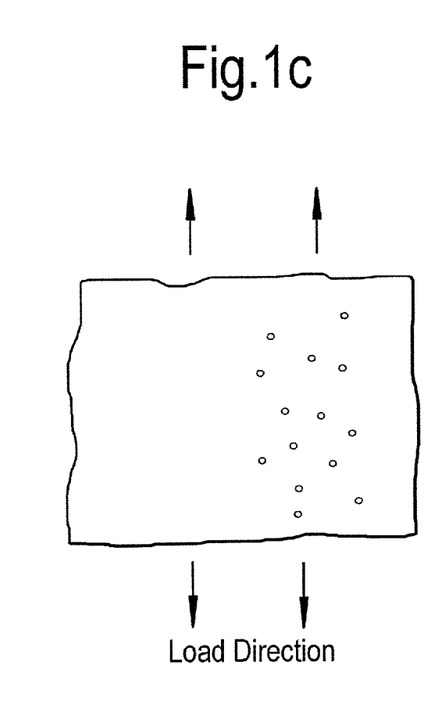
FIG. 1c is a schematic view of a material in which a plurality of voids is uniformly distributed within one half of the material.

FIGS. 1a to 1c show examples of the distribution of flaws in a material that might be considered to be acceptable by conventional "threshold size" or "total number" criteria, but would clearly not be acceptable in service.

FIG. 1a shows a material sample in which the flaws are aligned in a linear fashion across the material. This can result in cracks being likely to propagate between neighbouring flaws to produce a large crack and consequent fracture of the material.

FIG. 1b shows an arrangement where all the flaws in the material are clustered together in a single small region. This may have the effect that under any load conditions the material enclosed by the flaws is liable to crumble to create a single large flaw which in turn may result in structural failure of the material.

In FIG. 1c the flaws are present in one half of the material. This can result in the density of flaws (porosity) in that half of the material being approximately double the overall average flaw density. As a result, under uni-axial loading the material is liable to bend as well as extend.

One approach to assessing the distribution of flaws in a material to detect the presence of clustering would be to create an image of the material from a plurality of pixels and then to exhaustively examine each and every pixel, for example by using CT scanning techniques. This examination would indicate the presence of any flaw at a respective pixel.

A significant problem with the use of CT scanning techniques is that a single scan of a moderately sized component, such as a jet engine fan blade, can generate a vast quantity of data which in turn requires a huge image processing resource. This makes such techniques impractical for use as part of a routine QA process.

Figure 2:
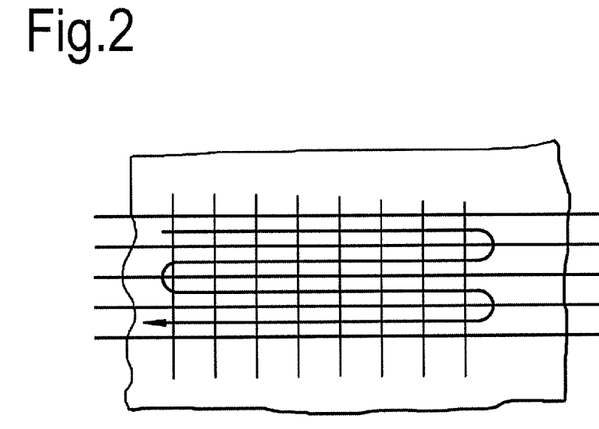
FIG. 2 shows a schematic view of a material comprising an array of pixels in which a path has been generated which passes through each one of the pixels.
Figure 3:
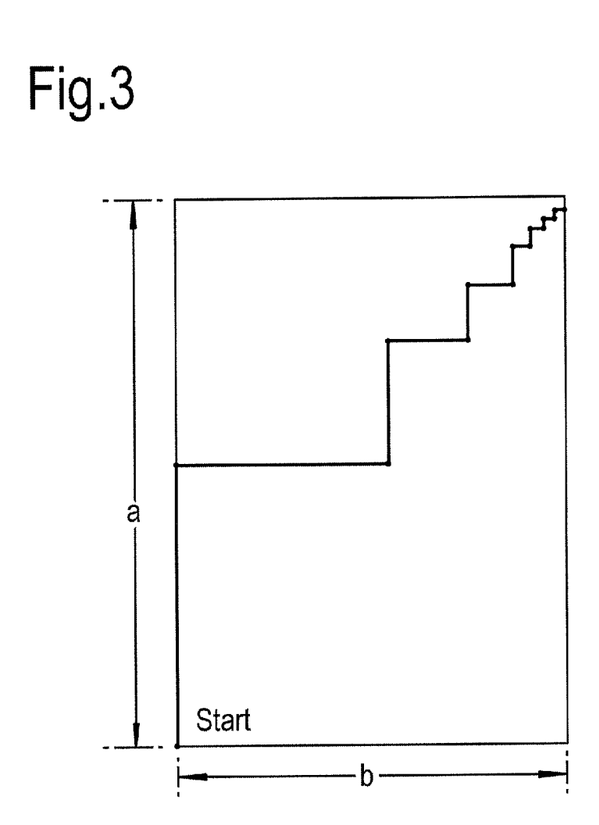
FIG. 3 shows an example of a two-dimensional path through a rectangular section of material in which the path comprises a plurality of path segments of varying length in terms of pixels.

An exhaustive examination would examine every pixel (as shown in FIG. 2) and rank each one as either having "good" material properties or having "flawed" material properties. It would then be possible to determine a measure of overall porosity on the basis of the numbers of "good" and "flawed" pixels.

However in order to be able to determine average flaw size, variations in local porosity or a measure of the clustering of any flaws, it is necessary to store and interrogate both the material property and the physical position of each pixel in the material. Given the quantity of data which is likely to be generated from even a small material sample, this will be a computationally difficult task. Such analysis is likely therefore to be extremely time-consuming and expensive.

There is therefore a need for a more efficient technique for analysing a material with a view to providing a measure not only of the overall quantity of flaws in the material but also their size and distribution.

STATEMENTS OF INVENTION

According to a first aspect of the invention there is provided a method for locating artefacts in a material, the method comprising the steps of:

(a) defining a path through a volume of the material;

(b) sensing the presence and type of any artefacts along the path;

and (c) determining, for each sensed artefact, the respective distance along the path.

The method provides an efficient means of assessing the statistical distribution of artefacts in a material, whether they be structural features of the material itself or defects in the material such as voids or inclusions.

By defining a path through the material which provides a statistically robust measure of the artefact distribution in the material, it is possible to effectively assess the suitability of the material for its intended purpose as part of a routine QA process.

An advantage of the method is that the material is analysed for the presence of artefacts only along the pre-defined path. It is therefore unnecessary to analyse every point within the material for the presence of artefacts.

This makes the method of the present invention more efficient and therefore cost-effective than conventional assessment methods which consider the entire volume of the material.

Optionally, the volume of material comprises a plurality of pixels and the path comprises a plurality of adjoining pixels.

The use of techniques such as, for example, computerised tomography enable the volume of material to be represented by a plurality of pixels.

Conventional analysis of such a representation of the volume of material would entail assigning a value to each pixel in the array, storing the resulting array of values and subsequently analysing the stored values to determine the quantity, size and distribution of any artefacts. As mentioned above, these steps are generally unsuitable for the routine analysis of parts from a manufacturing process.

Optionally, the path comprises X pixels, where X is a pre-defined integer, and the path comprises a plurality of adjoining path segments, with each path segment comprising a quantity of pixels within the range 1 to approximately (X/2).

The path segments comprise a range of lengths in terms of pixels. This enables an analysis of the quantity and size of any artefacts sensed in each of the path segments to provide information about not only the mean quantity of any such artefacts but also about their distribution throughout the volume of material.

In one embodiment of the invention, the plurality of path segments may be arranged in a reducing sequence in which each path segment is smaller than a preceding path segment. The reducing sequence may comprise a halving sequence (i.e. . . . 16, 8, 4, 2, 1), a reversed Fibonacci sequence (i.e. . . . 13, 8, 5, 3, 2, 1, 1) or any other reducing sequence.

In another embodiment of the invention, the path may comprise path segments having a predefined sequence, such as for example a Fibonacci sequence, but with the path segments ordered in a non-sequential manner (i.e. . . . 8, 13, 1, 5, 2, 1, 3).

Optionally, each path segment comprises a corresponding path segment vector which defines the orientation of the respective path segment within the volume of material, the vector sum of the path segment vectors defining the volume of material.

In one embodiment of the invention, the volume of material takes the form of a parallelepiped and the path is defined to extend between furthermost opposing corners of the volume. In this way, the vector sum of the individual path segments defines the parallelepiped.

In other embodiments of the invention, the volume may the form of an alternative three-dimensional figure, or polyhedron.

Optionally, the volume has a first length, a second length and a third length, a plurality of first path segments being oriented parallel to the first length, a plurality of second path segments being oriented parallel to the second length, and a plurality of third path segments being oriented parallel to the third length.

In an embodiment of the invention in which the volume is a parallelepiped, the volume is defined by first, second and third lengths which correspond to the three dimensions of the parallelepiped.

In other embodiments, where the volume is a higher order polyhedron, the volume may have fourth and/or higher order lengths with the path comprising corresponding higher order path segments.

The arrangement of the first, second and third lengths may define a symmetrical array of pixels. Alternatively, the array of pixels may be formed as an asymmetrical array.

Optionally, the path comprises a repeating path segment sequence of first, second and third path segments.

The repeating sequence of path segments which are oriented in each of the three dimensions of the parallelepiped ensures that the path includes a sample of pixels from each of the three dimensions.

Optionally, each of the first, second and third path segments is oriented orthogonally to one another.

In an embodiment of the invention in which the volume of material is represented by a regular parallelepiped, each of the first, second and third lengths will be oriented orthogonally to one another.

An advantage of the first, second and third lengths being oriented orthogonally to one another is that a repeating pattern made up of these orthogonal lengths can more easily be ordered so as to extend across the entire volume.

Optionally, each of the path segments is a linear path segment.

An advantage of each of the path segments being linear is that it simplifies the computational task of defining the path and the subsequent process of determining the distance along the path of any sensed artefacts.

Optionally, each of the first, second and third lengths is preferably at least 20 times, more preferably at least 200 times and most preferably at least 2000 times larger than a length of any sensed artefact.

The range of artefact sizes which are intended to be identified by the method is extremely large.

At one extreme this may include a particular crystal phase of a polycrystalline material, having a characteristic dimension of the order of tens of microns, or nano-particle additive materials (carbon nano-tubes, or clay particulates, etc.,) for use with composite resins. The term 'nano-' implies a particle size in the range 1 to $999 \times 10^{-9}$ m.

For example, a known problem with the inclusion of nano-particles in resin systems is that they tend to clump together and can be difficult to distribute uniformly across the resin. This makes cluster identification and measurement capability extremely important.

At the other extreme this could encompass voids within a composite material, or foreign body inclusions in, for example, a metallic cast component, which artefacts might measure several millimeters.

Optionally, each of the first, second and third lengths comprises N pixels, P pixels and R pixels respectively, where N, P and R are each pre-defined integers.

Optionally the method comprises the additional steps of:
(d) for each of the path segments, recording the total quantity of artefact pixels, being pixels which have been identified as corresponding to the presence of an artefact; and
(e) determining a representative artefact density for the volume of material based on the total quantity of the identified artefact pixels.

When determining a measure of the artefact density for the material, it is the absolute quantity of artefacts present in the material which becomes important rather than their size or distribution.

Optionally, the path comprises 2M path segments, where M is a pre-defined integer, the method comprising the additional steps of:
(f) for each of the M longest path segments, recording the quantity and location of any two or more consecutive artefact pixels, being pixels which have been identified as corresponding to the presence of an artefact; and
(g) for each of the two or more consecutive artefact pixels, determining a representative artefact dimension based on the quantity of the respective consecutive artefact pixels.

In order to provide a measure of the size of any artefacts identified in the material, it is necessary to consider path segments which are themselves longer than a dimension of the respective artefacts.

Optionally, the path comprising 2M path segments, the method comprising the additional steps of:
(h) for each of the M shortest path segments, recording the quantity of any artefact pixels, being pixels which have been identified as corresponding to the presence of an artefact; and
(i) determining a representative artefact distribution for the volume of material based on the total quantity of the identified artefact pixels.

Optionally, the method comprising the additional steps of:
(j) determining, for each length and orientation of path segment and for each of a pre-determined number of artefact types, the quantity of artefact pixels, being pixels which have been identified as corresponding to the presence of an artefact;
(k) determining, for each length and orientation of path segment and for each of a pre-determined number of artefact types, the quantity and lengths of any sequence of two or more consecutive artefact pixels;
(l) comparing the artefact pixel data derived in steps (j) and (k) to pre-determined values to provide a measure for the maximum artefact size and overall artefact density respectively for the volume of material;
(m) comparing the artefact pixel data derived in steps (j) and (k) to pre-determined values to provide a prediction of the strength of the material; and
(n) comparing the artefact size and density data and the strength prediction data derived in steps (l) and (m) respectively with pre-determined values to provide an indication of the material's serviceability.

In order for the method of the present invention to be useful as a QA technique in a manufacturing setting, it is necessary to be able to relate the artefact data (i.e. artefact density and size) to a corresponding change in a material property such as strength, toughness, etc.

By conducting a small number of validation analyses in which the volume of material is analysed in its entirety, rather than simply along the pre-defined path, it is possible to determine the influence of artefact size and density on fundamental material properties such as strength and toughness.

It then becomes possible to analyse volumes of the material using the method of the present invention and to relate the results obtained to changes in material properties. This allows the method to be used as a QA screening tool to identify 'reject' components in which the artefact size and density are such as to render the component unsuitable for its intended function.

Optionally, the method comprising the additional steps of:
(o) collating the data obtained in steps (j) and (k) by the orientation of the respective path segments;
(p) determining, from the collated data, a measure of the anisotropy in the artefact distribution and density;
(q) determining, from the collated data, a measure of the shape variations in the artefacts; and
(r) comparing the anisotropy and shape variation data derived in steps (p) and (q) respectively with pre-determined values to provide an indication of the material's serviceability.

By combining the artefact size and density data with the orientation of the path segments in which the artefacts have been identified, it becomes possible to obtain a measure of the distribution of the artefacts through the volume of material.

In this way, it is possible to obtain a measure of the clustering of the artefacts, for example as a variation in the artefact density through the volume.

Such variation in the artefact density through the volume can result in significant local variation in material properties. An example of this is shown in FIGS. 1a through 1c in which the distribution of artefacts results in local weakening of the material.

Other aspects of the invention provide devices, methods and systems which include and/or implement some or all of the actions described herein. The illustrative aspects of the invention are designed to solve one or more of the problems herein described and/or one or more other problems not discussed.

BRIEF DESCRIPTION OF THE DRAWINGS

There now follows a description of an embodiment of the invention, by way of non-limiting example, with reference being made to the accompanying drawings in which.

It is noted that the drawings may not be to scale. The drawings are intended to depict only typical aspects of the invention, and therefore should not be considered as limiting the scope of the invention. In the drawings, like numbering represents like elements between the drawings.

DETAILED DESCRIPTION

The use of composite materials for the manufacture of engineered components provides many advantages over the use of traditional materials such as metals. These advantages include, for example, increased strength/weight ratio and improved fatigue resistance.

However in order to realise these advantages it is necessary to ensure that the levels of artefacts in the component, which might have a deleterious effect on the material's properties, are kept below pre-determined values. Such artefacts may include features such as voids, air bubbles, areas of delamination or the inclusion of foreign bodies.

It is therefore necessary to monitor the level of artefacts in these components. This is generally achieved by means of a QA inspection process where each of the manufactured components is analysed to determine its suitability for use.

In a first embodiment of the invention (shown in FIG. 4) a section of a component is shown schematically as a square section of material and is designated generally by the reference numeral 10. The section 10 of material comprises a plurality of pixels 12 which are arranged as an array. The array 14 of pixels 12 is formed by means of computerised tomography.

Figure 4:
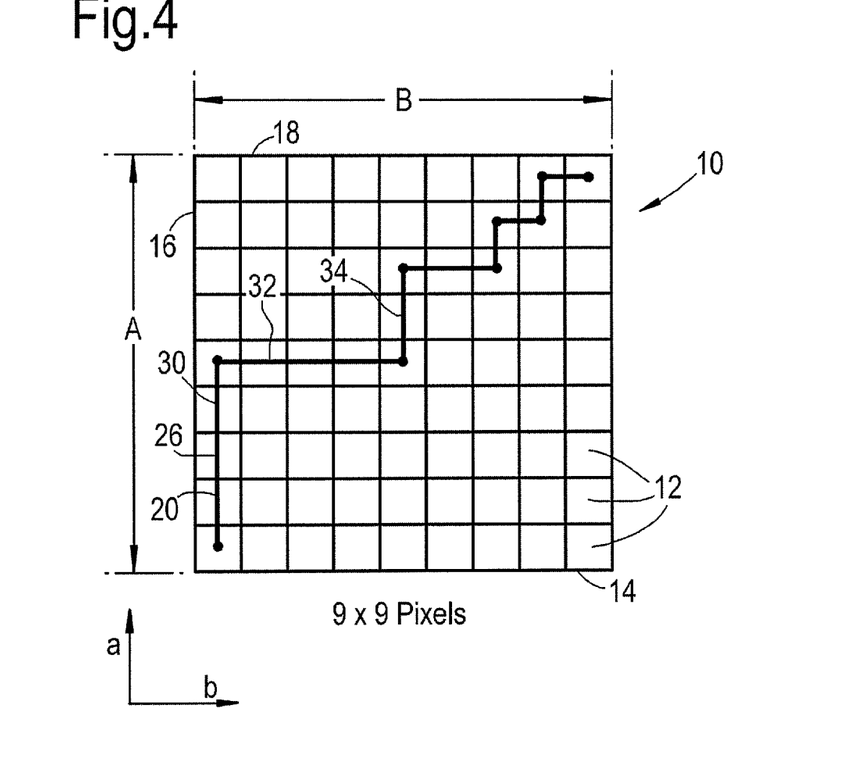
FIG. 4 shows an alternative arrangement of material section having a square array of pixels and where the path comprises path segments of varying length in terms of pixels.

Having formed the array of pixels 12, a path 20 is defined through the section of material with the path 20 comprising a plurality of adjoining pixels 12. The path 20 comprises a plurality of path segments 26 with the path 20 itself having a length of X pixels 12.

Each of the path segments 26 is defined as a linear group of pixels 12 with each path segment 26 having a length in the range of 1 pixel to (X/2) pixels 12.

It is possible to configure the array of pixels 12 in any convenient arrangement. One such arrangement involves sizing the array as a square array of side (2N+1) pixels 12, where N is an integer. This has the effect that, when using the above-mentioned technique for defining the path, the path 20 extends completely from one corner of the array 14 to an opposite corner of the array 14.

For a square array 14 of side length (2N+1), the path length will also be (2N+1) with the ratio of the path length to the total quantity of pixels 12 being $$\frac{1}{(2N+1)}.$$

In the example shown in FIG. 4, the array 14 is sized as a square array 14 of side (2N+1) pixels 12, in which N=4 thus generating a 9×9 pixel array 14.

In the embodiment shown, the path 20 is defined as starting from one corner of the array 14 of pixels 12 and extending across the array 14 to an opposite corner. The first path segment 30 extends from a corner of the array 14 along a first edge 16 of the array 14 and has a length equal to half the length A of the first edge 16 of the array 14. A second path segment 32 extends contiguously from the first path segment 30 and is oriented orthogonally to the first path segment 30 and parallel to a second edge 18 of the array 14. The length of the second path segment 32 is equal to half the length B of the second edge 18 of the array 14.

A third path segment 34 extends orthogonally from the end of the second path segment 32, i.e. parallel to the first path segment 30, and has a length equal to a quarter of the length of the first edge 16 of the array 14.

This arrangement of path segments 26 is then repeated with consecutive path segments 26 being oriented orthogonally to one another and the lengths of the path segments 26 being A/2, B/2, A/4, B/4, A/8, B/8, etc.

In this way the path 20 comprises a plurality of path segments 26 having between them a range of lengths in terms of pixels 12. This enables the inspection of the material to be carried out at multiple length scales which, as will be described in more detail below, enables the method of the present invention to detect and characterise not only artefact size and density but also artefact distribution (i.e. clustering).

Once the path has been defined, each pixel 12 along the path is analysed to determine if an artefact 40 (i.e. a void, inclusion or delamination) is present at that point in the material. Pixels 12 which correspond to the presence of an artefact 40 are termed artefact pixels 13. The result of this analysis is then stored for each pixel 12 along with the distance of the respective pixel 12 along the pre-defined path 20.

It is therefore not necessary to analyse the material at every pixel 12 within the array but only at those pixels 12 forming part of the pre-defined path 20. Consequently for the example of FIG. 4, it is necessary to only examine nineteen pixels from a total array quantity of eighty-one pixels.

When all the pixels 12 along the path have been analysed, the resulting data can then be processed to provide information about the artefact size, density and distribution in the material.

The total quantity of artefact pixels 13 identified along the path 20 taken as a ratio of the total quantity of pixels 12 along the path 20 can provide a measure of the overall artefact density for the material.

The longer of the path segments 26 (in this example, the first two path segments 30,32) are examined to determine whether there are two or more consecutive artefact pixels 13 which would indicate the presence of large artefacts 40. For each instance of two or more consecutive artefact pixels 13, the respective quantity of consecutive pixels 12 indicates the size of the artefact 40.

In addition, by comparing any instances of two or more consecutive artefact pixels 13 in the "a" direction with any such instances in the "b" direction, it is possible to obtain a measure of the differences in artefact distribution between the two directions.

The shorter of the path segments 26 (in this case the last six path segments) can then be examined to determine the quantity of any artefacts 40 in each path segments 26. The relative quantity of any artefacts 40 in the respective path segments 26 can provide an indication of the level of clustering of the artefacts 40, (i.e. variations in the artefact density).

The method may then be repeated using different sections of the material. These different sections may adjoin one another within the component, may follow contiguously or alternatively may overlap with one another.

Repeating the method using different starting points and/or different path orientations within the section of material ensures that the calculated artefact properties are statistically representative of the actual artefacts 40 present in the component.

Since the samples may be considered to be ergodic, the results obtained from the analyses in which the sections overlap with one another remain valid provided that the respective start point and initial path segment orientation differs between the overlapping sections.

The section may extend beyond the perimeter of the component in which case any pixels 12 falling outside the component are disregarded.

For any sample, multiple path investigations may be undertaken which will provide a statistical distribution of the quantities of consecutive artefact pixels 13 in the directions "a" and "b", and for different path segment lengths.

Taking an example in which the array 14 comprises a square array of 128 by 128 pixels and following the above-mentioned scheme for determining path segments lengths, provides for the first "a" and "b" segments being 64 pixels in length, the second "a" and "b" segments being 32 pixels in length, the third segments being 16 pixels in length, and so on.

In this example, if we consider an artefact size of five pixels, this artefact size is a small fraction of the first, second and third segments, and would be detected on the fourth segment (this being eight pixels in length). Thus for this size of artefact 40, we could get statistically similar data from an ensemble of equal path segment lengths from multiple path choices (i.e. using different start points in the sample). Comparing the statistics obtained from two different path segment lengths would reveal similarity, where the artefact size is much smaller than both segment lengths. This similarity would become less apparent as the artefact size approaches that of the shorter of the segment lengths.

The artefact data obtained from the analysis of a single path 20 can be expressed as a binary number where there is a single type of artefact 40, a ternary number where there are two types of artefact 40 and so on.

Taking an example in which a single type of artefact 40 is present, an analysis of the pixels 12 along the path 20 results in each pixel 12 being allocated a "0" if there is no artefact 40 present, and "1" if there is an artefact 40 identified. In a similar manner, the presence of other types of artefacts 40 may be denoted by allocating a "2", "3", "4", etc., in the number sequence representing the path segment analysis. For example, a path 20 having a length of nineteen pixels (see FIG. 5) and containing an artefact 40 of three pixels in length in the first "a" segment would be represented by the binary number 0111000000000000000. In representing in that form, it becomes clear that self-similarities at different length scales (powers of 2 (3, 4 etc)) can be explored by inspection, or computationally.

Following on from above, using multiple samples, the statistics of the "a" segments can be compared with those of the "b" segments. Where these are similar, it is clear that the artefact dimensions are similar in all directions, or that their alignment is random: meaning that the material property would remain isotropic. Where there are differences, then this would point to anisotropy in the artefact dimensions. Differences between the statistics for different length segments would differentiate the non spherical random artefacts from the spherical ones.

In a second embodiment of the invention (shown in FIG. 5) the section of material is shown as a three-dimensional volume and is designated generally by the reference numeral 100. Features of the section of material 100 which correspond to those of section 10 have been given corresponding reference numerals for ease of reference.

It is possible to configure the three-dimensional array 114 of pixels 112 in any convenient arrangement. However, extending the arrangement of the first embodiment to three dimensions results in the array being formed as a cubic array of side (2N+1) pixels 112, where again N is an integer. In the example shown in FIG. 5, the array 114 is sized as a cubic array of side (2N+1) pixels, in which N=1 thus generating a 3×3×3 pixel array.

Figure 5:
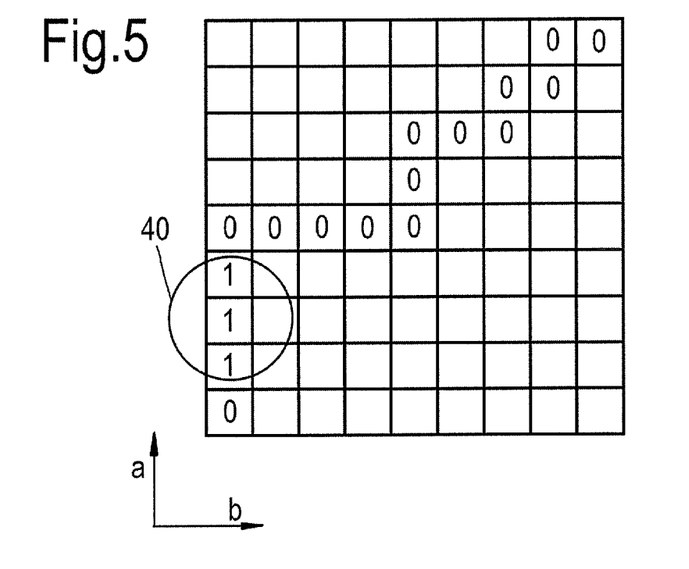
FIG. 5 shows a schematic representation of a path through an array of pixels representing a section of material showing a single circular artefact positioned in a single path segment.
Figure 6:
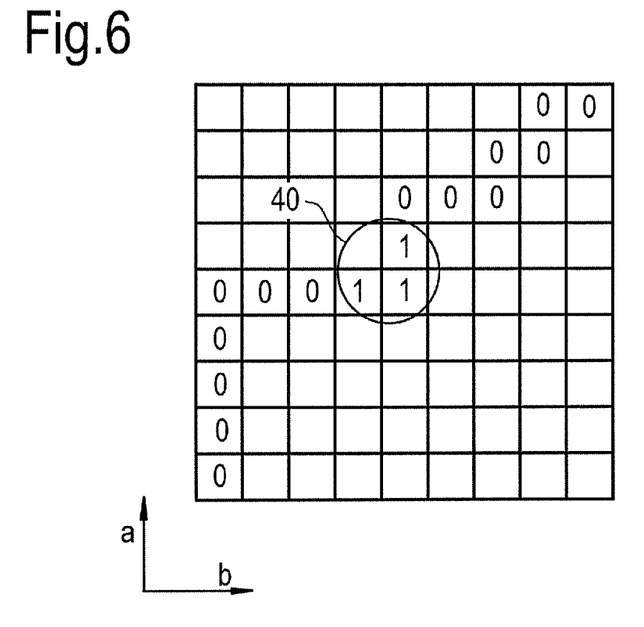
FIG. 6 shows a variant of FIG. 5 in which the single circular artefact is positioned across two path segments.
Figure 7:
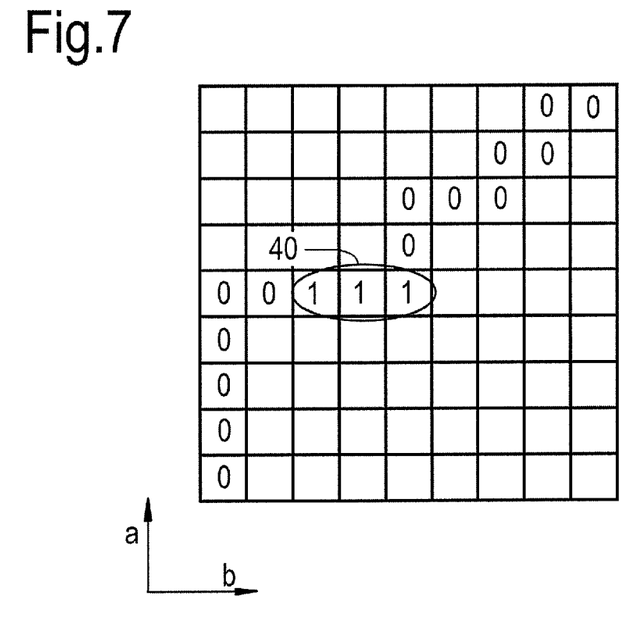
FIG. 7 shows a further variant of FIG. 5 in which the artefact is elliptical and positioned in a single path segment.
Figure 8:
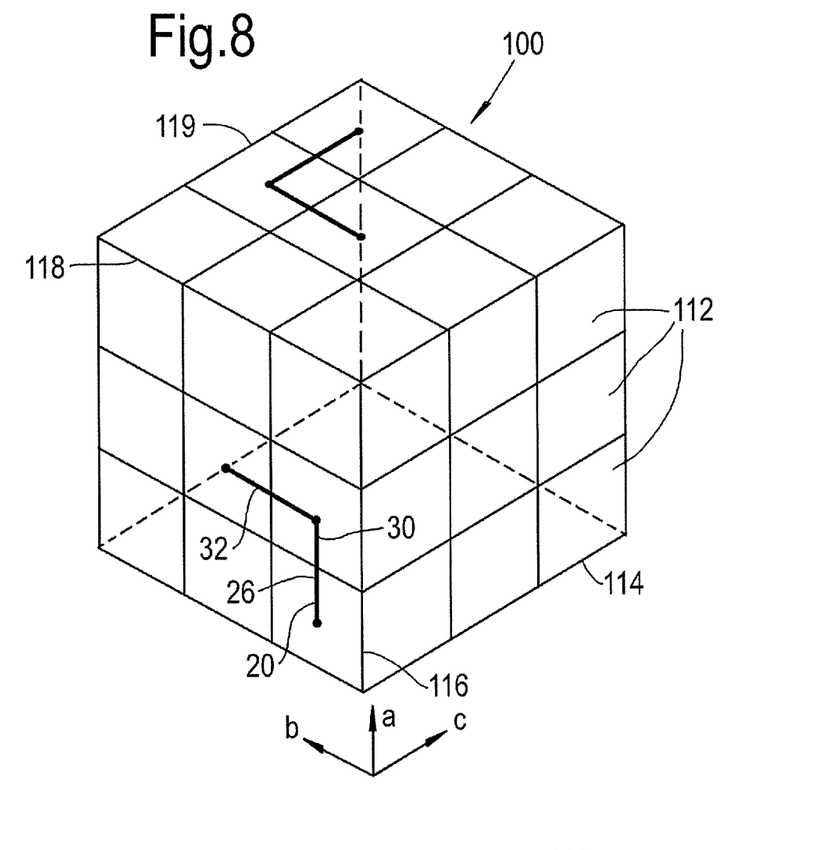
FIG. 8 shows a volume of material comprising a plurality of pixels and having a three-dimensional path defined through the material.

In the embodiment of FIG. 5, the path 20 is defined following similar rules to those described above with reference to the first embodiment. In other words, the first path segment 30 starts in one corner of the cubic array 114, extends along a first edge 116 of the array 114 and has a length equal to half the length A of the first edge 116 of the array 114.

A second path segment 32 extends contiguously from the first path segment 30 and is oriented orthogonally to the first path segment 30 and parallel to a second edge 118 of the array 114. The length of the second path segment 32 is equal to half the length B of the second edge 118 of the array 114.

A third path segment (not shown) extends orthogonally from the end of the second path segment 32, parallel to a third edge 119 of the array 114 and has a length equal to half the length C of the third edge 119 of the array 114.

This arrangement of path segments 26 is then repeated with respective consecutive path segments 26 being oriented orthogonally to one another, parallel to first, second and third edges of the array 116,118,119, and with the lengths of these path segments being A/2, B/2, C/2, N4, B/4, C/4, N8, B/8, C/8, etc.

In a similar manner to the first embodiment, a consequence of using the above-mentioned technique for defining the path 20 is that it extends completely from one corner of the array 114 to an opposite corner of the array 114.

For a cubic array 114 of side length (2N+1), the path length will also be (6N+1) with the ratio of the path length to the total quantity of pixels being $$\frac{(6N+1)}{(2N+1)^3}.$$

Consequently for the example of FIG. 5, by examining only the pixels 12 on the path it is necessary to only examine seven pixels from a total array quantity of twenty-seven pixels.

By greatly reducing the quantity of points within the material which must be analysed for the presence of artefacts 40, the method of the present invention provides significant computational savings over conventional prior art analysis techniques.

In addition, in the present method the properties of the material at each pixel 12 along the path 20 are stored along with the distance of the pixel 12 along the path 20. It is not necessary in the present method to store, for each pixel 12, the full-co-ordinates of respective pixels 12 within the material since the orientation of the path 20 is already known. This can provide a further saving in the computational requirements for implementing the present method over conventional material analysis techniques.

The method of the present invention has been described with reference to its use within an orthogonal x, y, z co-ordinate system. However, it is to be understood that the method is equally applicable to an alternative co-ordinate system, such as, for example, a cylindrical or spherical co-ordinate system.

In the embodiments described above, the present method has been applied to the analysis of data generated by the use of a non-destructive imaging technique such as ultrasound or computerised tomography.

In alternative third embodiment of the invention (shown as FIG. 9) the method may be applied to the use of a destructive analysis technique such as sectioning with the section of material being shown as a three-dimensional volume 200. Features of the section of material 100 which correspond to those of section 10 have been given corresponding reference numerals for ease of reference.

Figure 9:
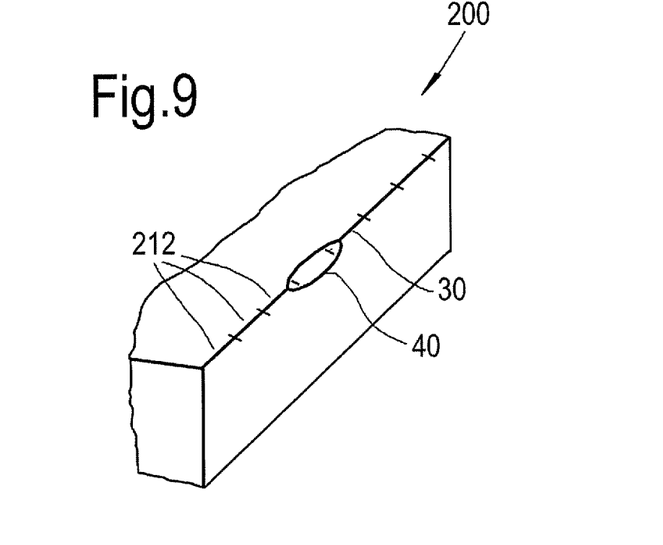
FIG. 9 shows a schematic representation of a material sample which has been sectioned and in which the revealed cut edge represents a path through the material.

In this embodiment, the component is sectioned, say at a mid-point or other region of interest to produce two halves of the component. One of these halves is discarded and the second is sectioned again.

This second sectioning process produces a cut edge which can be considered as a first path segment 30 which can be defined as comprising one or more pixels 12. The analysis techniques described above with reference to the first two embodiments of the invention can therefore be applied to the analysis of this path segment 30.

Once analysed, the remaining piece of the component is sectioned again, and one half discarded. The new cut edge is then considered as analogous to the second path segment, again comprising one or more pixels 12, and is analysed as outlined above.

This sectioning process is then continued until the remaining portion of the component is too small to analyse for the presence of artefacts. The results obtained from the analysis of the cut edges may then be analysed to provide an indication of the size, density and clustering of any artefacts 40.

The method of the present invention has been described with reference to the analysis of laminated composite materials. However it is to be understood that the invention may be embodied in other specific forms (for example, the analysis of the crystal phases within a poly crystalline material) without departing from its essential characteristics.

The described embodiments are to be considered in all respects only as illustrative and not restrictive. The scope of the invention is therefore indicated by the appended claims rather than by the foregoing description. All changes which come within the meaning and range of equivalency of the claims are to be embraced within their scope.

What is claimed is:

1. A method for locating artefacts in a material, the method comprising the steps of:
   (a) defining a volume of the material, the volume having a first length, a second length and a third length;
   (b) obtaining an image of the volume, the image comprising a plurality of pixels;
   (c) defining a path through the image, the path comprising a plurality of adjoining pixels;
   (d) defining the path as comprising a repeating sequence of adjoining first path segments, second path segments and third path segments, the first path segments being oriented parallel to the first length, the second path segments being oriented parallel to the second length, and the third path segments being oriented parallel to the third length;
   (e) for each pixel along the path, analysing a pixel parameter to sense if the pixel represents an artefact; and
   (f) determining, for each sensed artefact, a respective distance along the path to the corresponding pixel.

2. The method as claimed in claim 1, the path comprising X pixels, X being a pre-defined integer, and wherein the path comprises a plurality of adjoining path segments, each path segment comprising a quantity of pixels within the range 1 to approximately (X/2).

3. The method as claimed in claim 2 wherein each path segment comprises a corresponding path segment vector which defines the orientation of the respective path segment within the image of the volume of material, the vector sum of the path segment vectors defining the image of the volume of material.

4. The method as claimed in claim 1 wherein each of the first, second and third path segments is oriented orthogonally to one another.

5. The method as claimed in claim 2 wherein each of the path segments is a linear path segment.

6. The method as claimed in claim 4 wherein each of the first, second and third lengths is at least 20 times larger than a length of any sensed artefact.

7. The method as claimed in claim 4 wherein each of the first, second and third lengths comprises N pixels, P pixels and R pixels respectively, where N, P and R are each pre-defined integers.

8. The method as claimed in claim 1, the method comprising the additional steps of:
   (g) for each of the path segments, recording the total quantity of artefact pixels, being pixels which have been identified as corresponding to the presence of an artefact; and
   (h) determining a representative artefact density for the volume of material based on the total quantity of the identified artefact pixels.

9. The method as claimed in claim 1, the path comprising 2M path segments, M being a pre-defined integer, the method comprising the additional steps of:
   (i) for each of the M longest path segments, recording the quantity and location of any two or more consecutive artefact pixels, being pixels which have been identified as corresponding to the presence of an artefact; and
   (j) for each of the two or more consecutive artefact pixels, determining a representative artefact dimension based on the quantity of the respective consecutive artefact pixels.

10. The method as claimed in claim 1, the path comprising 2M path segments, the method comprising the additional steps of:
    (k) for each of the M shortest path segments, recording the quantity of any artefact pixels, being pixels which have been identified as corresponding to the presence of an artefact; and
    (l) determining a representative artefact distribution for the volume of material based on the total quantity of the identified artefact pixels.

11. The method as claimed in claim 1, the method comprising the additional steps of:
    (m) determining, for each length and orientation of path segment and for each of a pre-determined number of artefact types, the quantity of artefact pixels, being pixels which have been identified as corresponding to the presence of an artefact;

(n) determining, for each length and orientation of path segment and for each of a pre-determined number of artefact types, the quantity and lengths of any sequence of two or more consecutive artefact pixels;

(o) comparing the artefact pixel data derived in steps (m) and (n) to pre-determined values to provide a measure for the maximum artefact size and overall artefact density respectively for the volume of material;

(p) comparing the artefact pixel data derived in steps (m) and (n) to pre-determined values to provide a prediction of the strength of the material; and (q) comparing the artefact size and density data and the strength prediction data derived in steps (o) and (p) respectively with pre-determined values to provide an indication of the material's serviceability.

12. The method as claimed in claim 11, the method comprising the additional steps of:

(r) collating the data obtained in steps (m) and (n) by the orientation of the respective path segments;

(s) determining, from the collated data, a measure of the anisotropy in the artefact distribution and density;

(t) determining, from the collated data, a measure of the shape variations in the artefacts; and (u) comparing the anisotropy and shape variation data derived in steps (s) and (t) respectively with pre-determined values to provide an indication of the material's serviceability.

* * * * *